(12) United States Patent
Brunetto Tancredi

(10) Patent No.: US 11,850,358 B2
(45) Date of Patent: Dec. 26, 2023

(54) SMART CONTROL SYSTEM AND METHOD BASED ON MACHINE LEARNING FOR MODULATING END-TIDAL CONCENTRATION LEVELS BY MEANS OF ADJUSTMENTS TO THE VOLUME AND CONCENTRATION OF AN INCOMING RESPIRATORY GAS FLOW IN REAL TIME

(71) Applicant: SOCIEDADE BENEFICENTE ISRAELITA BRASILEIRA HOSPITAL ALBERT EINSTEIN, São Paulo (BR)

(72) Inventor: Felipe Brunetto Tancredi, São Roque (BR)

(73) Assignee: SOCIEDADE BENEFICENTE ISRAELITA BRASILEIRA HOSPITAL ALBERT EINSTEIN, São Paulo Sp (BR)

(*) Notice: Subject to any disclaimer, the term of this patent is extended or adjusted under 35 U.S.C. 154(b) by 1083 days.

(21) Appl. No.: 16/471,365

(22) PCT Filed: Dec. 19, 2017

(86) PCT No.: PCT/BR2017/050389
§ 371 (c)(1),
(2) Date: Jun. 10, 2020

(87) PCT Pub. No.: WO2018/112588
PCT Pub. Date: Jun. 28, 2018

(65) Prior Publication Data
US 2020/0368464 A1    Nov. 26, 2020

(30) Foreign Application Priority Data
Dec. 19, 2016    (BR) ...................... 10 2016 029897 0

(51) Int. Cl.
*A61M 16/00*    (2006.01)
*G16H 40/63*    (2018.01)
(Continued)

(52) U.S. Cl.
CPC ........ *A61M 16/0003* (2014.02); *G16H 40/63* (2018.01); *A61M 2016/003* (2013.01);
(Continued)

(58) Field of Classification Search
CPC .............. A61M 16/024; A61M 16/026; A61M 16/0003; A61M 16/0051;
(Continued)

(56) References Cited

U.S. PATENT DOCUMENTS 6,889,691 B2    5/2005    Eklund et al.
7,066,173 B2    6/2006    Banner et al.
(Continued)

OTHER PUBLICATIONS

International Search Report dated Mar. 21, 2018 in International Application No. PCT/BR2017/050389.
(Continued)

*Primary Examiner* — Kendra D Carter
*Assistant Examiner* — Mautin I Ashimiu
(74) *Attorney, Agent, or Firm* — B. Aaron Schulman, Esq.; Stites & Harbison, PLLC

(57) ABSTRACT

In accordance with the present disclosure, a system and method of intelligent control is provided that is based on machine learning, to modulate end-tidal concentration levels through continuous adjustments in the volume and concentration of a flow of incoming respiratory gases. The system and the method are able to continually estimate and adjust new gas flows that are administered for a user to inhale in immediate future moments of inspiration, based on the concentration and pressure signals collected at the actual moment of breathing and at previous moments of breathing, (Continued)

without the need for reservoirs to store inspired or expired gases, or for aprioristic physiological models.

27 Claims, 1 Drawing Sheet

(51) Int. Cl.
| | |
|---|---|
| *A61M 16/10* | (2006.01) |
| *G16H 20/40* | (2018.01) |
| *A61B 5/00* | (2006.01) |
| *A61B 5/0205* | (2006.01) |
| *A61B 5/083* | (2006.01) |
| *A61B 5/087* | (2006.01) |
| *G16H 50/20* | (2018.01) |
| *A61B 5/08* | (2006.01) |

(52) U.S. Cl.
CPC . *A61M 2205/3331* (2013.01); *A61M 2230/04* (2013.01); *A61M 2230/432* (2013.01); *A61M 2230/435* (2013.01); *A61M 2230/50* (2013.01); *A61M 2230/63* (2013.01)

(58) Field of Classification Search
CPC ........... A61M 16/202–204; A61M 2016/0027; A61M 2016/006; A61M 2016/0033–0039; A61M 2016/102; A61M 2016/1025; A61M 2205/3331; A61M 2016/103; A61M 2205/3344; A61M 2230/432; A61M 2230/435; A61M 16/021; A61H 2230/40; A61H 20/40; A61B 5/082; A61B 5/087; A61B 5/7264; A61B 5/7267; Y10T 137/2499
See application file for complete search history.

(56) References Cited

U.S. PATENT DOCUMENTS

| | | |
|---|---|---|
| 2015/0173647 A1 | 6/2015 | Orr et al. |
| 2016/0158481 A1* | 6/2016 | Klein ................. A61M 16/026 128/203.14 |

OTHER PUBLICATIONS

Translation of International Preliminary Report on Patentability dated May 22, 2019 in International Application No. PCT/BR2017/050389.

* cited by examiner

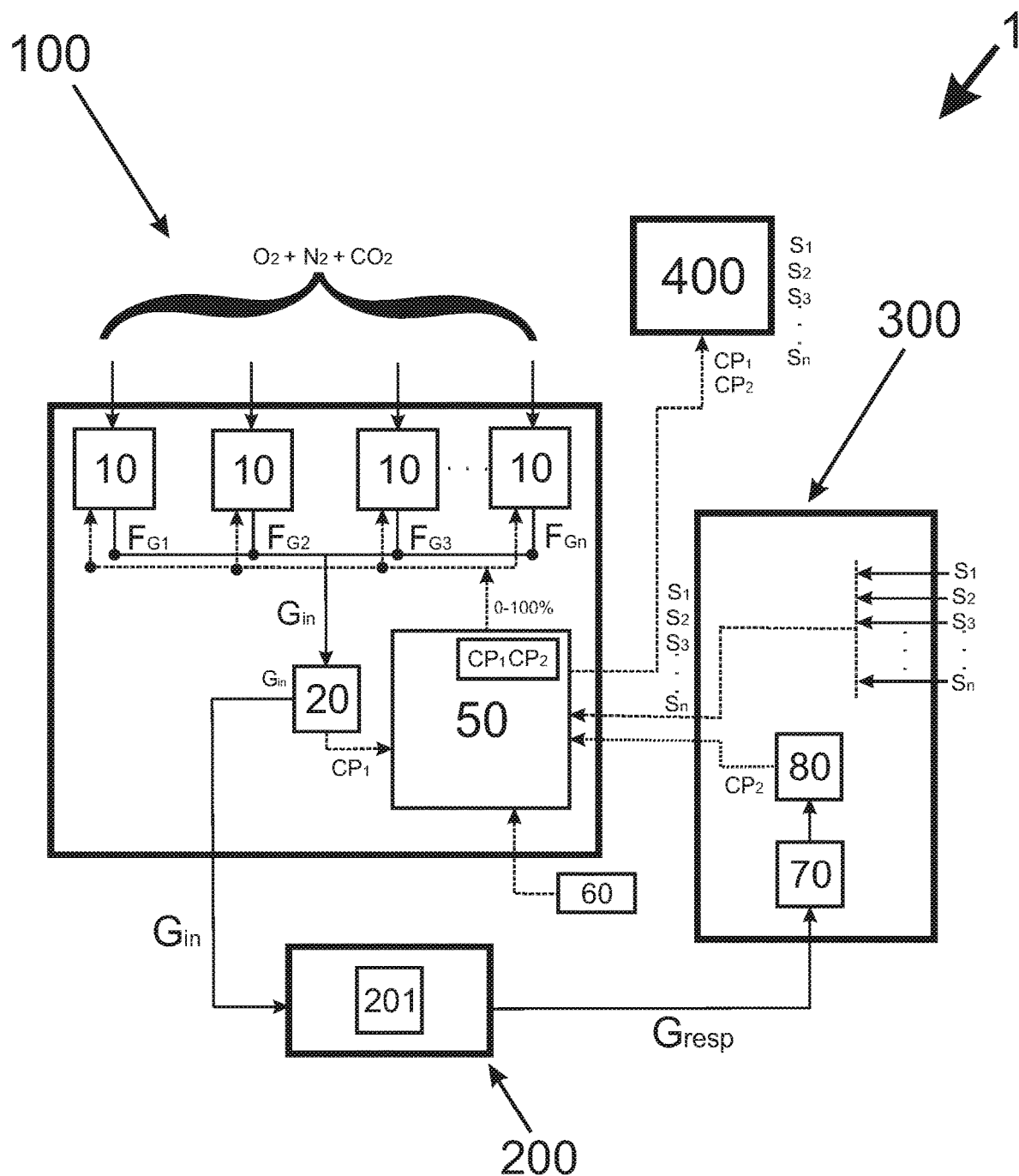

SMART CONTROL SYSTEM AND METHOD BASED ON MACHINE LEARNING FOR MODULATING END-TIDAL CONCENTRATION LEVELS BY MEANS OF ADJUSTMENTS TO THE VOLUME AND CONCENTRATION OF AN INCOMING RESPIRATORY GAS FLOW IN REAL TIME

The present invention refers to a system and intelligent control method, based on machine learning, to modulate oxygen levels and end-tidal carbonic gas (measured at the end of the expiratory cycle) in a precise manner, independently of an operator, performing adjustments in real time to the volume and concentration of mixtures of O2, CO2 and N2 that are administered for inspiration. The system and the method is able to continually estimate and adjust new gas flows that are administered for a user to inhale in immediate future moments of inspiration, based on the concentration and pressure signals collected at the actual moment of breathing and at previous moments of breathing, without the need for reservoirs to store inspired or expired gases, or for aprioristic physiological models

DESCRIPTION OF THE STATE OF THE ART

Alterations in the levels, or partial pressures, of arterial O2 and CO2 (PaO2 and PaCO2) function as a respiratory and cardiovascular stimulus. PaCO2 and PaO2 are directly related to the partial concentrations/pressures inspired of the respective gases as well as the total volume inspired per unit of time. Respiratory maneuvers altering the volume and/or concentrations inspired are widely used in studies and examinations of ventilatory and cardiovascular responses.

A simple way to obtain modulations in the levels of O2 and CO2 is to modify inspired volume, for example, performing an apnoea. With the cessation of gas exchanges between the lungs and the external environment, the alveolar levels, and, thus, the CO2 and O2 arterial levels alter. Due to the impossibility of replacing the O2, the PaO2 decreases; and due to the impossibility of eliminating the CO2, the PaCO2 increases.

An equally simple maneuver to alter levels of respiratory gases in the blood without the use of equipment is hyperventilation, which, by increasing the rate of gas exchanges between the lungs and the external environment, leads to opposite results of those of apnea, namely: that the PaO2 increases and the PaCO2 decreases.

An alternative to altering the PaO2 and PaCO2 through the use of rudimentary equipment is re-breathing, which does not necessarily manipulate the total volume of gases inspired, but rather the partial concentrations/pressures inspired. With this maneuver, the subject inspires previously exhaled gases that are stored in an expiration reservoir and have O2 concentrations below normal and CO2 concentrations above normal. Thus, the maneuver generates a combined stimulation of hypercapnia (PaCO2 above the normal physiological level, measured in a resting state) with hypoxia (PaO2 below the normal level).

The maneuvers described above, although simple and widely available, have their disadvantages; the most significant of these is the impossibility of manipulating the levels of O2 and CO2 independently, which hinders examinations requiring one of the controlled variables to study the effect of one of these gases exclusively. Other disadvantages include: dependence on the co-operation of the subject in following the apnea or hyperventilation instructions (which, it may be said in passing, renders studies/examinations on unconscious patients unfeasible); a limitation on the PaO2 and PaCO2 levels that can be achieved; low reproducibility of the stimulus; and, in the case of re-breathing, possible discomfort on breathing newly exalted gases, whose temperature is higher than that of the ambient air (considered "fresh").

The other way to manipulate PaCO2 and PaO2 is through the administration of "fresh" gaseous mixtures for inspiration, with partial pressures of O2 and CO2 different from that of the atmospheric air. For example, the inspiration of gases with partial pressures of O2 lower than the atmosphere generates hypoxia; the inspiration of gases with partial pressures of O2 higher than the atmosphere generates hyperoxia (PaO2 greater than the normal physiological levels). Similarly, the administration of gases with a small amount of CO2 for inspiration reduces the efficiency of eliminating this gas through the lungs and generates hypercapnia. Hypocapnia can only be generated through hyperventilation.

Since the partial pressures of arterial O2 and CO2 (PaCO2 and PaO2) are closely related to the partial pressures of CO2 and O2 measured at the end of the expiratory cycle (end-tidal), it is possible to use PetCO2 and PetO2 (which are easily measured and monitored) as a reliable indicator of PaCO2 and PaO2.

The simplest way to manipulate PetO2 and PetCO2 using gaseous mixtures is to administer fixed concentrations of these gases for inspiration. However, this method has its limitations, such as the difficulty in achieving specific levels of PetCO2 and PetO2, and controlling them independently.

In addition, the levels of arterial/end-tidal O2 and CO2 depend on the concentrations and volumes inspired—as mentioned earlier—and also on the subject's physiology. A given concentration of inspired O2 can raise the end-tidal levels to different levels depending on the subject and the situation, which limits the reproducibility of the stimulus.

Moreover, the end-tidal levels take a long time to stabilize after a change in the inspired levels, often not even stabilizing within a time interval of an imaging examination of the vascular response. This may not be a big problem for examinations based on the acquisition of high temporal resolution, but it prejudices measurements requiring longer observation windows.

No less important is the variation in the ventilatory response associated with the manipulation, also specific to each subject, which disrupts the control over the end-tidal levels. For example, a manipulation inducing hypercapnia with administration of an atmospheric air mixture with 5% CO2, which has practically the same concentration of O2 that we normally breathe—approximately 21%—usually leads to an increase in the inspired volume, which results in increased levels of PetO2 (as in the case of hyperventilation described above). The increase in PetO2 due to the hypercapnic stimulus prevents more definite conclusions regarding the independent effect of PetCO2 on the system examined (whether respiratory or cardiovascular). Moreover, changes in the velocity of exchanges between the lungs and the external environment interfere with the transfer of the levels of modulated PetCO2, creating another source of variability.

Hyperoxia, hypercapnia, hypoxia, or hypocapnia that are induced to generate effects for diagnostic purposes should constitute transient and benign disturbances. The inspiration of elevated CO2 levels leads to hypercapnia, which, if maintained for a long period, generates acidosis—an undesirable situation. Severe and prolonged hypoxia can have irreparable effects.

A fairly simple way to control the administered volume which is inspired by the subject—which is to say, the dose—and thus to minimize the interference of the gas whose stimulus is not the object of study, is to use partial re-breathing. The technique proposed by Harvard researchers in 2000 (Banzett R B, Garcia R T, Moosavi S H. Simple contrivance "clamps" end-tidal PCO(2) and PO(2) despite rapid changes in ventilation. J Appl Physiol. 2000 May; 88(5):1597-600) is very useful for circumventing the problem of ventilatory response, but does not, in itself, allow for the achievement of specific levels in the manipulated gases.

To achieve specific levels quickly and to enable their maintenance during a given period, it is necessary to administer O2 and CO2 concentrations that are varied throughout the manipulation; not only during the moments of transition, to accelerate the rise or fall of the end-tidal levels to the desired levels—as also realized by the Harvard researchers—but also after the rise or fall, to ensure the maintenance (stability) of the end-tidal levels.

In 1982, researchers from the University of Oxford (Robbins P A, Swanson G D, Micco A J, Schubert W P. A fast gas-mixing system for breath-to-breath respiratory control studies. J Appl Physiol. 1982 May; 52(5):1353-62) presented an elegant technique for performing modulations in CO2 and O2 in a predictable and independent manner. The technique used an aprioristic physiological model to predict the behavior of the alveolar/end-tidal gases in response to the concentrations inspired; and used feedback to correct the table of values of the concentrations that should be inspired in later cycles. The concentrations inspired varied according to the predictive table and were adjusted to each respiratory cycle, depending on the last end-tidal values monitored. The flow administered was fixed and should be greater than the peak of inspiration. It was possible to keep the PetO2 constant and at the same time produce waveforms in PetCO2 very close to the desired shape. However, it was difficult to achieve specific levels of these gases because, for example, the model required an estimate of the volumes inspired—which represented a gain in the proposed algorithm. These parameters were initially defined and, throughout the examination, manually adjusted by the operator, by trial and error. To achieve specific end-tidal levels the system of "waveform control" depended on manual adjustments; which is to say, it was not an automatic control mechanism.

In 2007, another group from the University of Oxford (Wise R G, Pattinson K T S, Bulte D P, Chiarelli P A, Mayhew S D, Balanos G M, et al. Dynamic forcing of end-tidal carbon dioxide and oxygen applied to functional magnetic resonance imaging. J Cereb Blood Flow Metab. 2007 Aug. 1; 27(8):1521-32) proposed a system for controlling end-tidal levels of O2 and CO2 based on feedback gain control, i.e. input adjustment (i.e. partial inspired pressures) through feedback of the output readings (i.e. end-tidal partial pressures). It was demonstrated that the system made it possible to achieve specific levels of PetCO2 and PetO2, and keep them stable for a certain period, but only after a transitional period that presented considerable instability (overshoots followed by oscillations). Perhaps as a result, the system's ability to perform modulation in end-tidal levels by following more complex waveforms has not been demonstrated.

The adjustment of the concentrations was done based on the readings of PetCO2 and PetO2 taken at the end of the immediately previous expiratory cycle, which is to say, at a single moment of measurement and during a single cycle. In addition to this, the inspired concentrations were adjusted between one inspiration and another, not in the same inspiratory cycle.

Moreover, the system required the certainty that the concentrations inspired were equal to the concentrations administered. This required a specific breathing apparatus, in this case, a mouthpiece; and the administration of a high volume of gases, such as the method proposed in 1982, in order to ensure that the flow of gases administered was always greater than, or equal to, the inspired flow (greater than the maximum peak of inspiration), which increased the operational costs involved—a factor that may have ended up rendering the propagation of the method unviable.

The above method was subsequently perfected by a group of researchers from the University of British Columbia (Koehle M S, Giles L V, Curtis A N, Walsh M L, White M D. Performance of a compact end-tidal forcing system. Respir Physiol Neurobiol. 2009 Jun. 30; 167(2):155-61) which sought to reduce the volume of gases administered/consumed using a simple calculation of the inspired volume; and applied an attenuation factor to avoid overshoots and transient instabilities of the end-tidal response. The volume of inspired gases was estimated based on the volume inspired measured in the immediately preceding cycle through the integration of the signal read by a flow sensor; and an extra volume was added as a safety mechanism to prevent choking. The gases were administered in an inspiration reservoir and the remaining gases invariably contaminated the dose administered in the subsequent cycle. This, in addition to the attenuation factor, prevented the rapid transition (in less than 2 respiratory cycles) between end-tidal levels and the production of more complex waveforms.

Recently, researchers at the University of Toronto (Slessarev M, Han J S, Mardimae A, Prisman E, Preiss D, Volgyesi G, et al. Prospective targeting and control of end-tidal CO2 and O2 concentrations. J Physiol (Lond). 2007 Jun. 15; 581(Pt 3):1207-19) proposed a system for controlling end-tidal levels based on a comprehensive physiological model of gaseous exchanges between lungs, the external atmosphere and the blood—also described in the publication of a patent application PCT No. WO2014194401A1—and which was subsequently refined to use feed-back monitoring of the end-tidal levels achieved [described in U.S. Patent Application No. US 2016/0158481]. The system uses a sequential respiratory circuit (physical or virtual) analogous to that proposed by the Harvard researchers for controlling inspired volume (by partial re-breathing), which allows for a reduction in the volume of gases administered compared to the techniques of the Oxford researchers.

It has been shown that the system is capable of achieving and maintaining specific levels of PetCO2 and PetO2 reasonably well; and that it performs complex modulations in the end-tidal levels in a given range of values. However, it is not so clear that the algorithm is capable of achieving specific levels in a wide range of possibilities. For example, in the literature it is common to find the device manipulating PetCO2 levels between 40 mmHg and 45 mmHg PetCO2, a range in which the behavior of gaseous exchanges is more easily monitored; and producing square waveforms. When it comes to more sophisticated examinations, the waveforms obtained in research laboratories are not so well behaved (Halani S, Kwinta J B, Golestani A M, Khatamian Y B, Chen J J. Comparing cerebrovascular reactivity measured using BOLD and cerebral blood flow MRI: The effect of basal vascular tension on vasodilatory and vasoconstrictive reactivity. NeuroImage. Elsevier Inc; 2015 Feb. 4; 1-14).

Like the Oxford model of 1982, the model requires initial estimates of physiological parameters—higher than those required by the former. The mass balance equations used in the aprioristic model have more than 3 dozen terms.

Several of the constants on which the aprioristic predictive model is based must be estimated and indicated by the operator at the beginning of the manipulation. It is also noted that the impact of all possible choices on the end-tidal results obtained was not demonstrated.

Another disadvantage is that, according to the guidance given by the manufacturer the subject examined should be instructed to empty the gas reservoir administered from the physical sequential breathing circuit with each inspiration.

The use of the sequential circuit seeks to ensure that a given, fixed dose (volume/concentration) is inspired during a given inspiratory cycle. The dose is administered during the first moment of the inspiratory cycle and then a certain amount of neutral gases (or at least which do not have the purpose of manipulating the alveolar gases) ideally at a volume equal to or greater than the dead volume, flows into the administration device. There is no adjustment of the volume/concentration during the phase of the administration of the effective dose for manipulation.

In the case of the use of the virtual sequential circuit [described in U.S. patent application No. US 2016/0158481], it is necessary to monitor the volumes inspired during a plurality of inspiratory cycles using a flowmeter to determine the threshold, at which time the change in the concentration of gases occurs in a given inspiratory cycle. No continuous analysis is performed of the dose ratio (volumes and concentrations administered) and end-tidal responses obtained in previous respiratory cycles.

There are other patent documents which describe techniques for the modulation of respiratory gases, such as the publication of the international patent application PCT No. WO 2013042024, which reveals a system that seeks to maintain a constant basal flow, but with varied partial pressures (concentrations), thus making it possible to simulate variations in the concentrations of $O_2/CO_2/N_2$ observed in the cycles of human respiration.

It is observed, however, that this document refers to a breathing simulator, which is not used, therefore, to induce anything in patients. The document reveals a technique for testing equipment, not to be used in examinations for evaluating the cardio-vascular condition.

Despite being similar to the present invention, since it reveals an injection of gases with continuous monitoring of partial pressures, it is observed that this does not describe, or suggest mechanisms, for modulating end-tidal concentrations, or the use of machine learning for such.

Another document is Brazilian patent application BR PI0313823-2, which proposes the use of fuzzy logic in the work calculation for the administration of gases to a patient. The method was developed for use in ventilatory support equipment—i.e. it is dedicated to varying the volume and total air pressure administered to the patient to effect natural ventilation in the unconscious patient. The system and method do not have the functionality of modulating the inspired/expired gases, nor do they include an analysis of expired gaseous concentrations. A major conceptual difference in relation to the present invention is the fact that the technique does not adapt the optimum pressure during the ventilation procedure, which is to say, the calculation is done and the ventilatory maneuver set in the ventilator at the beginning of the procedure, based on previously prospected clinical data. In addition, this document does not describe use for cardio-respiratory testing purposes, for example.

By contrast, the present invention varies the volume of the respiratory gases administered, regardless of their concentrations, with a view to monitoring the volume of the patient's inspiration during its normal breathing in order to deliver the exact amount of gases needed to fill its lungs without the need for a flowmeter. When, at times, a slightly higher volume of gases is administered, it has the purpose of compensating for instrumental problems/particularities, such as leaks in the mask/circuit employed in the delivery of the administered gases. In other words, the technique is not intended to vary the pressure of the gases administered to force the breathing of the subject or patient under ventilatory support. Ideally the system should be able to deliver the exact amount of gas at every moment in time in order to ensure that the pressure within the gas administration device is null in relation to the ambient air pressure; and that there is no contamination of the gases administered by gases which may, by chance, enter the device through damaged edges or valves.

During inspiration, the pressure within the device tends to fall below ambient air pressure, which is immediately compensated by the administration of a certain volume of gas that is sufficient to cause the pressure within the device to remain null. However, in some devices with leaking edges, vents without valves or with unefficient unidirectional valves, there may be a flow of gases from outside into the administration device, especially during the first phase of the inspiratory cycle, which leads to contamination of the flow of gases administered by ambient air and the compromising of the control of the manipulation. In such cases, a flow of gases slightly higher than necessary to meet the inspiratory need of the subject is administered, in order to generate positive pressure within the device (relative to ambient air pressure) and to ensure that the flow of gases will always be from the inside out.

To perform the end-tidal modulations, the concentrations of the respiratory gases in the mixtures flowing to the administration device (mask or respiratory circuit) are varied, but independently of the flow, and without the need for data prior to the examination, in order to work. Although not mandatory, previous data from prior examinations, in the same or in other patients, may be used to further improve the calculation of new mixtures to be administered/inspired to achieve the desired end-tidal levels. Machine learning (convergence on the solution) happens faster.

The publication of the international patent application PCT No. WO2014194401 reveals a system for the control of gaseous concentrations where modulations are obtained through the administration of predetermined quantities/doses of gases, calculated using an aprioristic model, with feedback from the reading of the end-tidal concentrations for automatic adjustments of the model and the respective doses that were initially calculated. The control of the gases is achieved in an essentially different manner from the present invention: by feed-forward, based on stoichiometric equations intended to describe the physiology of the target.

The system described in document WO2014194401 also does not perform or use readings of total pressure of the respiratory gases.

It is also noted that the delivery of the gases is achieved "discretely", with doses (i.e. volumes and concentrations) fixed in each inspiratory cycle, and that are not continuous, as in the present invention, where both the volume and the concentration of the gases administered are adapted and vary within the same inspiratory cycle.

For the correct functioning of the system revealed in document WO2014194401, the system possesses a threshold mechanism (mechanical valves) to ensure the inspiration of a fixed volume of the administered concentrations, which is followed by a variable volume of gas considered "neutral". It is observed that, for the correct functioning of the control method, the patient needs to breathe all the volume administered in the cycle, and that the volume of neutral gas should be greater or equal to the dead volume.

However, it is noted that inspired volumes less than the administered volume may compromise the results, since part of the administered volume remains in the inspiration reservoir contaminating the new gases administered during later cycle(s). This is a problem, especially for examinations requiring rapid changes in the concentrations/volumes inspired. To avoid this problem, when using the sequential circuit for the administration of gases, subjects are usually instructed to observe the inspiration reservoir and, consciously, empty it during each cycle.

The system described in WO2014194401 is configured to manipulate the concentrations inspired only during the first phase of the inspiratory cycle, after the air is sent to the inspiration reservoir, with no possibility of altering it, which prevents the optimal use of the inspiratory cycle to perform rapid manipulations and may pose a problem when the respiratory rate and minute volume are highly irregular.

It is also worth remembering that "dead volume" is a physiological concept, where lungs and airways are treated as an ideal sequential circuit. Dead volume includes airways and alveolar spaces where gaseous exchanges are low due to obstruction and/or low blood perfusion. Dead volume can diminish when, for example, cardiac output increases and alveoli begin to receive more blood; or increase, when, for example, the inspiratory volume increases and starts to refill other alveoli with low blood perfusion. Thus, dead volume cannot be treated as a fixed volume; it must be seen as a dynamic volume. No end-tidal control method based on aprioristic models (like the method described in WO2014194401) incorporates dead volume as a variable. And the failure to adapt to this dynamic may compromise control over the end-tidal levels and the efficiency of the manipulation.

Another important point is that for the manipulation to occur correctly and only during the first phase of the inspiratory cycle, the system described in WO2014194401 uses a specific respiratory circuit (sequential and with a rebreathing reservoir).

Moreover, for the operation of the method, it is necessary, at the start of the manipulation, to inform the system of the different anatomical/physiological parameters that represent constants in the stoichiometric equations of the physiological model, most of which are only crudely estimated by the operator.

By contrast, the present invention allows the manipulation of gases inspired throughout the inspiratory cycle. As the gases are supplied on demand, it may be noted that there is no need to inspire a minimum amount of gases or follow ventilation instructions. This allows manipulations to be performed even on unconscious patients. Conscious subjects/patients are also free to breathe spontaneously during the procedure.

By performing continuous variations in the inspired dose (i.e. both the volume and concentration of the gases), the system confers greater efficiency on the control, i.e. the desired end-tidal levels are achieved quickly and making optimum use of the gases.

Another advantage lies in the fact that a machine learning-based control algorithm can compensate for dynamic effects of the different lung volumes, such as the dead volume. It is not that the "dead volume" is a variable that is explicitly treated, but a control based on machine learning can take into account the different associations between the physiological monitoring data and the results obtained. For example, the algorithm is able to learn the exact effect of the depth of inspiration and cardiac output in the relationship between gases inspired during the last phases of the inspiratory cycle and the end-tidal variation produced by them.

Additionally, it is observed that the present invention allows for the use of different types of breathing devices, since the system and method that are the object of the present invention perform the administration of respiratory gases in an adaptive way and through learning, taking into account any disturbances in the breathing device, such as leaks and the malfunctioning of any of its components; inspiratory thresholds; and even re-breathing.

Finally, it is highlighted that the end-tidal concentration control technique presented here is not based on a physiological model, or on any aprioristic function, but rather on an artificial intelligence algorithm. In contrast to other classic control systems, this system is based on machine learning, a type of adaptive control that dispenses with knowledge about how the various input variables of the system are actually related in order to generate its output. This type of control dispenses with the indication of starting parameters and is self-calibrating, which is to say, it does not depend on constants set by an operator and its "action plan" is adapted for each patient and each set of conditions. Even more importantly, the control mechanism improves with the time of use: either over one or more examinations on the same patient or with use on several patients; and even by "talking" (sharing network learning data) with other units/equipment of the same model (operating in accordance with the concept of cloud robotics). In other words, the performance of its control over the levels of end-tidal oxygen and carbon dioxide improves with the time of use of the system, as well as the time of use of other units of the same model that connect to it in a network.

Considering the above techniques, it is observed that none of them proposes a system based on machine learning, capable of modulating specific levels of PetO2 and PetCO2 in a fast, precise, independent and reproducible manner; without the need for control over the inspired volume, or for calibration by the estimated physiological parameters, and is, thus, independent of the operator; and, finally, independent of the subject's cooperation.

Moreover, no system is observed in the state of the art for the administration of gases on demand that enables the optimization of the use of gases without the use of re-breathing (and dedicated respiratory circuits), or any other reservoir, thus preventing the risk of interference of expired gases in previous cycles as well as of gases administered in previous cycles, thus increasing the efficiency of the manipulation. A system capable of controlling the volume and the concentration of gases administered in real time, thus allowing for the variation of the doses inspired in the same inspiratory cycle increases the possibilities for control over the prospected end-tidal levels.

Similarly, no system is observed in the state of the art based on machine learning that allows for the generation of rapid and precise modulations in the end-tidal levels and which can be used in different studies of respiratory and cardiovascular physiology, having a special function in studies of cerebral neurovasculature and metabolism by magnetic resonance imaging.

Cerebral vasculature is extremely sensitive to variations in PaCO2 (much more so than PaO2) and everything indicates that it may be possible to evaluate the functional status of the neurovasculature through the neuroimaging measurement of its vasodilatory and vasoconstrictive response to variations in PaCO2 levels, especially using the MR technique, which offers excellent spatial resolution and makes it possible to evaluate responses in the different segments of the vasculature: from the major arteries to the capillary vessels. Recent studies have shown that not only the breadth, but the speed of the vascular response, also provides important information about its state of health. Moreover, vascular response may vary according to the levels (high or low) of manipulated PaCO2. A wide range of hypercapnic/hypocapnic stimuli, covering different intervals of PetCO2, have been used to study the reactivity of the vasculature of the brain to CO2.

Recently it has been proposed that CO2 modulations combined with modulations in O2, would make it possible to quantify not only the vascular response to these gases, but also the levels of gas exchanges between the blood and tissues, i.e. respiration, or cellular, aerobic metabolism—a very important measurement for understanding health, disease and the aging of the brain. A system that allows for the modulation of PetCO2 and PetO2 independently, producing complex waveforms that are easily reproducible, and that performs its function automatically, making optimum use of gases, would be of great value in this field.

The aforementioned method is based on image measurements of the physical and physiological effects deriving from modulations in the concentrations of blood CO2 and O2, but the imaging techniques used have limited sensitivity. Gaseous modulations with a lower level of spurious variations produce an image with lower noise and greater power of detection of the associated responses, i.e. greater sensitivity. By allowing precise control of the end-tidal levels, the present invention helps to improve the quality of this valuable imaging method.

Comparing the measurements of vascular reactivity and metabolism depends on the reproducibility of the method, which in turn depends on the reproducibility of the underlying stimulus, namely: modulations in the arterial O2 and CO2 levels. The system and method of control of end-tidal levels described herein should contribute to the adoption of these measurements in clinical practice.

Finally, a system and method for respiratory control based on feedback but able to adapt to the physiological status of the user in real time and using the history of stored data is not observed in the state of the art. The present invention allows for an adaptation of the levels of gases to be administered in any type of user, in a single examination, and throughout the duration thereof, in real time, using data collected over the course of the respective examination, and even previously, from the same user or any other population.

Similarly, a system and method for controlling respiratory gas levels based on machine learning and whose control is improved with the time of use is not observed in the state of the art.

Moreover, a system for controlling respiratory gases capable of adapting the flow of gases administered to the type of device used in the delivery of gaseous mixtures (mask/circuit) is not observed.

OBJECTIVES OF THE INVENTION

A first objective of the present invention is to provide a system and a method of intelligent control, based on machine learning, capable of automatically manipulating levels of respiratory gases using monitoring data concerning pressure and the respective concentrations of O2 oxygen and CO2 carbonic gas, and other auxiliary physiological variables, without the need to use a physiological, deterministic, aprioristic model based on stoichiometric equations, but rather using an adaptive computational model based on artificial neural networks and fuzzy logic.

A second objective of the present invention is to provide a system and a method of control, based on machine learning, capable of achieving the first objective above, by sending gases on demand to a user in a way that i) optimizes the consumption of gases without the use of inspiration reservoirs or direct flow measurement II) optimizes the manipulation of inspired concentrations and thus performs faster modulations at the expired levels and III) allows the user to perform neuroimaging tests naturally, not dictated by a given speed, inspiratory depth or any other instructions imposed by the operator.

A third objective of the present invention is to provide a system and a method of control, based on machine learning, able to respond to the physiological status of the user in real time, without the need for anatomical/physiological parameters estimated by the operator, or for clinical data collected previously from a population.

A fourth objective of the present invention is to provide a system and a method of control, based on machine learning, capable of being used with a variety of mask types and respiratory circuits without the need to use a specific device for the administration of the gaseous mixtures.

BRIEF OF THE INVENTION

The objectives of the present invention are achieved through an intelligent control system, based on machine learning, to modulate end-tidal concentration levels through continuous adjustments to the volume and concentration of a flow of incoming respiratory gases; the system is configured to sample and measure, in real time, a first concentration and pressure signal from the flow of incoming gases administered in a breathing device at a current breathing moment and a second concentration and pressure signal from a flow of respiration gases within the breathing device in the current breathing moment, the system being configured to estimate, in real time, and based on the first and second concentration and pressure signals measured in the current breathing moment and in concentration and pressure signals measured in previous breathing moments, a new volume and a new concentration of oxygen and carbonic gas for the flow of incoming gases for an inspiration moment in the immediate future, the immediate future moment of inspiration occurring after the current breathing moment, the system being configured to adjust the volume and concentration of oxygen and carbonic gas of the incoming gas flow several times within the same inspiratory cycle.

The objectives of the present invention are also achieved by means of an intelligent control method, based on machine learning, to modulate end-tidal concentration levels through continuous adjustments to the volume and concentration of a flow of incoming respiratory gases, the method comprising the stages of:

A) continuously sampling and measuring a first concentration and pressure signal from the flow of incoming gases administered in a breathing device at a current breathing moment;

b) continuously sampling and measuring a second concentration and pressure signal from a flow of respiration gases within the breathing device in the current breathing moment;

c) estimating, based on the signals sampled and measured in steps a) and b) and in concentration and pressure signals measured at previous respiration moments, a new volume and a new concentration of oxygen and carbonic gas for the flow of incoming gases for an inspiration moment in the immediate future; and d) adjusting the volume and concentration of oxygen and carbonic gas of the flow of incoming gases within the same inspiratory cycle.

BRIEF DESCRIPTION OF THE DRAWINGS

The present invention will be described in more detail below based on one example of execution represented in the drawings. The figures show:

FIG. 1—is an illustration of the control system for manipulating the levels of respiratory gases evidencing the elements that compose it and the fluidic and electrical connections.

DETAILED DESCRIPTION OF THE INVENTION

In order to overcome the problems faced by the techniques developed in the state of the art, the present invention was developed. As previously mentioned, the present invention refers to a method and a control system for generating specific modulations in the levels of expiratory gases.

It is observed that FIG. 1 illustrates the system that is the object of the present invention and the elements that compose it, which are a module for administering the gases 100, a breathing device 200 and a monitoring module 300.

In a preferred configuration, the gas administration module 100 is endowed with a plurality of flow controllers 10, a first oxygen and carbon dioxide concentration and pressure sensor 20 and a control unit 50.

The flow controllers 10 of the gas administration module 100 are electromechanical devices equipped with a valve, the latter being configured to be fully or partially open according to the electrical signal received. In a general sense, the valves of the flow controllers 10 may open in such a way as to allow different gas flows to be obtained. Merely by way of example, if the flow controllers 10 have an operating range of between 0 and 5 VDC, they remain closed when the signal is 0 VDC and remain fully open (maximum gas flow) when the signal is 5 VDC. With the aim of not limiting the use of the flow controllers 10 with a specific operating range, it is observed that, henceforth, it will only be affirmed that the flow controllers 10 have levels of gradation between 0% (totally closed) and 100% (fully open). Preferably, the plurality of flow controllers 10 should present an operating response of a maximum of 10 milliseconds (ms) for a 90% opening. It should be noted that this is only a preferred example, such that any other fast-acting flow controllers may be used, provided that they minimize delays in the control system.

Moreover, in a preferred configuration, the plurality of flow controllers 10 is individually fed with a mixture composed of oxygen O2, nitrogen N2 and carbonic gas CO2 in different proportions. It may also be noted from FIG. 1 that when each flow controller 10 is activated, it generates at least one flow of flow gases FG1, FG2, FG3, FGn, which converge on each other, in order to form a flow of incoming gases Gin, which flows to the first oxygen and carbonic concentration and pressure sensor 20, as shall be described below. The activation and individual control of each of the controllers 10 is carried out by the control unit 50. It is important to highlight that the mixing chamber must be positioned as close as possible to the breathing device 200, thus minimizing the delay in the delivery of the mixtures.

In relation to the first concentration of oxygen and carbon dioxide and pressure sensor 20 of the gas administration module 100, it is observed that it is equipped with transducers configured to transform the measurements of the concentration of oxygen O2 and carbon dioxide CO2 into electrical signals.

The first concentration of oxygen and carbonic gas and pressure sensor 20 is also equipped with a transducer capable of transforming gas pressure levels into electrical signals.

As can be seen from FIG. 1, the flow of incoming gases Gin formed by at least one flow of flow gases FG1, FG2, FG3, FGn generated by each flow controller 10 is received by the first oxygen and carbon dioxide concentration and pressure sensor 20. This performs measurements of the concentration levels of oxygen and carbonic gas, and the pressure of the flow of incoming gases Gin, and sends them to the control unit 50. The measurements performed by the first sensor of the concentration of oxygen and carbonic gas and pressure 20 are henceforth referred to as a first concentration and pressure signal CP1. As shall be described below, the flow of incoming gases Gin is subsequently sent from the first sensor of the concentration of oxygen and carbonic gas and pressure 20 to the breathing device 200.

Like the first sensor 20, the second sensor of the concentration of oxygen and carbonic gas and pressure 80 is equipped with transducers configured to transform the measurements of oxygen O2 and carbon dioxide CO2, and pressure into electrical signals.

The second sensor of the concentration of oxygen and carbonic gas and pressure 80 is also equipped with a transducer capable of transforming gas pressure levels into electrical signals.

The measurements performed by the second sensor of the concentration of oxygen and carbon dioxide, and pressure 80, are henceforth referred to as a second concentration and pressure signal CP2.

Preferably, the first and second sensors of the concentration of oxygen and carbonic gas 20 and pressure 80 are equipped with transducers capable of presenting concentration readings in less than 150 milliseconds (ms). Even more preferably, in the case of the oxygen transducers, these should have a short response time, to achieve a 90% final reading in a time of less than 130 milliseconds (ms); in the case of carbon dioxide transducers, these should present a response time of less than 50 milliseconds (ms). It should be noted that this is only a preferred example, so that any transducers/sensors of action/rapid reading may be used, provided that they minimize delays in the control system.

With respect to the control unit 50 of the gas administration module 100, it is observed that this is an electronic device equipped with processors, controllers, memories or any other electronic component, capable of coordinating and controlling all the elements of the system of the present invention. The control unit 50 is responsible for the initialization of the system, sending signals to activate and control the flow controllers 10, reception and storage of the concentration signals of the oxygen O2 and carbon dioxide CO2, and pressure CP10 and CP20, measured at a current breathing moment T0, the concentration signals of oxygen O2, carbon dioxide CO2 and pressure CP1$n$, CP2$n$ measured at previous breathing moments T-n, reception and storage of electrical and non-electrical signals relating to the physiological parameters S1, S2, S3, Sn of a user 201 in the current moment of respiration T0 and in previous moments of respiration T-n, interface with the system operator and use of an artificial intelligence algorithm for predictive calculation to manipulate the levels of respiratory gases to be administered/inspired by the user 201, through the activation of the control of the flow controllers 10.

It should be noted that the physiological parameters S1, S2, S3, Sn are parameters collected from the user 201, such as thoracic expansion, volume of inspired and expired gases, electromyography, pulse oximetry, heart rhythm, humidity of the respiratory gases, ECG signal, blood pressure, arterial blood velocity, blood gas analysis and pH, temperature, electrical conductance of the skin, but not limited to these.

As will be described in due course, the physiological parameters S1, S2, S3, Sn can be used as additional variables to further improve the predictive calculation for manipulation of the levels of respiratory gases to be administered/ inspired by the user 201, and are, thus, not indispensable to this calculation.

Of course, the physiological parameters S1, S2, S3, Sn above are only examples, not constituting, as a result, an obligation or limitation of this system. The system operator can select other physiological parameters S1, S2, S3, Sn not foreseen above, according to the examinations to be performed and if it understands that these additional variables will improve the predictive calculation for the adjustment of the respiratory gas levels to be administered/inspired by the user 201 in order to achieve the desired modulation in the end-tidal levels.

Additionally, the control unit 50 can store anthropometric, demographic and population data in its memory, to be used individually or in conjunction with the physiological parameters S1, S2, S3, Sn. The use of such data does not represent an obligation or limitation of this system, being used only so that the predictive calculation for manipulation of the levels of respiratory gases to be administered/inspired by the user 201 is further improved.

Moreover, in a preferred configuration, it is observed that the breathing device 200, illustrated in FIG. 1, is a mask/ breathing circuit equipped with an inlet and an outlet, respectively, to enable the user 201 to inhale and exhale gases.

It should be noted that a variety of types of breathing devices 200 can be used by the present invention, ranging from a simple mask without gas leakage control to a more complex mask with leakage control, valves in the inlet and outlet, respiratory circuits with inspiration/expiration reservoirs and even bacterial filters. The fact that different breathing devices 200 can be used is due to the fact that this system uses a control method capable of adapting to potential interferences in the system, such as leaks and contamination of the mixtures administered by gases accumulated in inspiration/expiration reservoirs, and by machine learning, estimating new and future flows of incoming gases (Gin) necessary to compensate for such interferences. The control realized by this system and method will be detailed below.

Also, in reference to the breathing device 200, it may be noted that this receives, in its inlet, the flow of incoming gases Gin, which flow is inspired by the user 201 by means of the breathing device 200. After the inspiration, the user 201 will expire the gases. As previously noted, depending on the type of breathing device 200 used and its insulation from the exterior, part of the gases administered (flows of incoming gas, Gin) may leak. Thus, part of the gases administered/ inserted into the breathing device 200 may not be inspired. The expired gases, in turn, are sent from the interior to the outlet of the breathing device 200.

It is important to highlight that the breathing device 200 is fluidically connected to a gas sampler 70 of the monitoring module 300, which is responsible for the sampling of the pressure and concentration of the gases inspired and/or expired by the user 201. The concentration measurement is achieved through suction, from the breathing device 200 to the oxygen concentration and carbonic gas sensors 80. It is observed that the gases inspired and/or expired by the user 201 will henceforth be termed the respiration gas flow Gresp, which are the gases contained inside the breathing device 200 and suctioned by the gas sampler 70.

As a result of the gas suction for concentration sampling by the sensors 80, the volume of gases administered is adjusted to deliver the amount of gases which flow to the sensors 80 in addition to the volume required to meet the inspiratory need of the user 201.

In a preferred configuration, a mixing chamber (not shown) is positioned at the inlet of the breathing device 200, the mixing chamber being configured to receive at least one flow of flow gases FG1, FG2, FG3, FGn that form the flow of incoming gases Gin. Alternatively, the mixing chamber can be positioned in the gas administration module, immediately after the outlet pipes of the flow controllers 10. It should be noted that the pipes used should have a minimum internal volume, with the objective of minimizing delays in the control system.

Also alternatively, but not obligatorily, a bacterial filter can be positioned at the inlet of the breathing device 200. Additionally, in an alternative and non-mandatory character, the breathing device 200 may have fluidic connections with sources of oxygen gases and compressed air for the administration of gases in case of emergency and stand-by state, respectively. In addition, the breathing device 200 may comprise valves controlled by the control unit 50, for the selective activation and deactivation of the sources of oxygen and compressed air gases.

As can be seen from FIG. 1, the gas sampler 70 is fluidically connected to the second oxygen and carbonic gas concentration and pressure sensor 80.

Alternatively, a bacterial filter may be positioned at the outlet of the breathing device 200 and at the inlet of the gas sampler 70.

As previously noted, the breathing device 200 receives at its inlet the flow of incoming gases Gin. The gases which flow into the breathing device 200 are called respiration gas flow Gresp, and may comprise gases inspired or expired by the user 201.

As can be seen from FIG. 1, the respiration gas flow Gresp which flows from the gas sampler 70 is received by the second oxygen and carbon dioxide concentration and pressure sensor 80. This then performs measurements of the levels of concentration of oxygen and carbon dioxide, and the pressure of the respiration gas flow, and sends them to the control unit 50.

Depending on the moment of the respiratory cycle when the measurement is performed, the oxygen and carbon dioxide concentration and pressure sensor 80 can, for example:

i) measure the concentration and pressure of gases inspired by the user 201, if the measurement is performed during the inspiratory cycle; or II) measure the concentration and pressure of the gases expired by the user 201, if the measurement is performed during the expiratory cycle.

Given that the system and method that are the object of the present invention perform calculations of the volume and concentration of the incoming gas flow Gin in real time, it is observed that both measurements mentioned above, the concentration and pressure of the Gin gases and the concentration and pressure of the Gresp gases, will be realized in a cyclical manner, which is to say, continuously.

For example, initially, the respiratory gas flow (Gresp) will comprise the inspired gases. In this case, the system and method will estimate and adjust the volume and concentration of the incoming gas flow (Gin) taking into account the measurements of the Gin and Gresp gases within the respective inspiratory cycle.

Considering that an inspiratory cycle is followed by an expiratory cycle, it is observed that, in a second moment, the respiratory gas flow (Gresp) will involve the expired gases. In this case, the system and method will estimate the volume and concentration of the incoming gas flow (Gin) at an immediate future moment of inspiration T1 taking into account the measurements of the Gresp gases realized within the respective expiratory cycle, as well as any other measurements of concentration and pressure of Gin and Gresp realized in respiratory cycles prior to this.

The second oxygen and carbon dioxide concentration and pressure sensor 80 performs the CP2 measurements of the Gresp respiration gases circulating within the breathing device 200, and after the measurements, if the respiration gas flow (Gresp) comprises expired gases, these will be sent into the atmosphere.

Having described the elements that compose the system of the present invention individually, the electrical and fluidic connections between them will duly be described.

As can be seen from FIG. 1, the flow controllers 10 of the gas administration module 100 are equipped with pipes for fluidic connection with cylinders (not shown) containing oxygen O2, carbonic gas CO2 and nitrogen N2, in different proportions. Each of the flow controllers 10 is also equipped with outlet pipes for the flow of flow gases FG1, FG2, FG3, FGn, and these outlet pipes converge on a central pipe. The latter is fluidically connected to the first oxygen and carbon dioxide concentration and pressure sensor 20.

It is also observed that each of the flow controllers 10 is electrically connected to the control unit 50, the latter being responsible for sending individual signals to each controller 10 with gradation levels between 0% (fully closed) and 100% (fully open). It should be noted that the pipes used must have a minimum internal volume, with the objective of minimizing delays in the control system.

In relation to the first oxygen and carbon dioxide concentration and pressure sensor 20, it is noted that it samples the flow of incoming gases (Gin) from the central pipe. The central piping is fluidically connected to the breathing device 200. The first oxygen and carbonic gas concentration sensor 20 is also electrically connected to the control unit 50, so that the latter receives the first concentration and pressure signal CP1. It is also observed that the control unit 50 is electrically connected to the control buttons 60, so that the system can be duly activated and disabled in case of emergency or if the operator desires. It should be noted that the pipes used should have a minimum internal volume, with the objective of minimizing delays in the control system.

As previously described, the breathing device 200 establishes a fluidic connection with the user 201, which inspires the gas flow (Gresp), which is ideally formed only by the incoming flow (Gin) that is administered in the respiratory device 200. In relation to the expired gases (also called the respiration gas flow or Gresp) and as previously highlighted, the breathing device 200 collects, through its outlet, all or part of the gases expired by the user 201.

In relation to the electrical connections, it is observed that the second oxygen and carbon dioxide concentration and pressure sensor 80 is connected to the control unit 50, so that the latter receives the second concentration and pressure signal CP2. The control unit 50 also receives physiological parameters S1, S2, S3, Sn, originating from sensors and/or transducers connected to the user 201 and processed by means of dedicated digital signal processing devices.

Additionally, the control 50 unit is connected to a data display center 400, responsible for providing the operator with the concentration and pressure signals CP1 and CP2 and the physiological parameters S1, S2, S3, Sn. Alternatively, the control unit 50 can display, in addition to the current user data 201, signals measured at previous moments of respiration T-n, forming a trace of the history of the monitored signals, as well as signals that are predicted by the algorithm for later moments (real-time updated traces); and a comparison between the traces, namely: the desired end-tidal concentration signals and those obtained via monitoring (whose deviation from the desired standard should be minimal).

Having described the electrical and fluidic connections between the elements of the system that is the object of the present invention, the methodology used in this system will be described below.

The methodology of the present invention uses an artificial intelligence algorithm, through a closed loop control, adjusting the volume and concentration of the flow of incoming gases (Gin) to be administered in the breathing device 200 and then inspired by the user 201 in the form of Gresp in order to generate a given pattern of expiratory response.

Furthermore, the proposed system and methodology are intended to control end-tidal/blood/alveolar gases using intelligent, machine-learning-based control, which is a smart algorithm that relies on machine learning, which can be based on artificial neural networks, evolutionary algorithms, reinforcement learning, among others. Artificial neural networks can also be combined with fuzzy logic to generate control of the Neuro-Fuzzy type.

It is observed that the present control methodology allows the concentrations of expiratory gases of part or even of the entire expiration cycle to be modulated without the need for an explicit modeling of the associations between these and the inspired gases. The output of the system is controlled from an action planned in the input (pressure and concentration of incoming gases Gin) that is based on a statistical analysis of the existing association between input, output (i.e. concentration signals measured during the expiratory cycle, but above all those measured at the end of it, i.e. end-tidal levels) and other feedback signals (including all the other pressure and concentration signals, and physiological monitoring signals S1, S2, S3, Sn).

It is worth noting that the oxygen and carbon dioxide concentration and pressure signals CP1, CP2 collected in real time in the current respiration cycles T0 and CP1$n$, CP2$n$ collected in previous respiration cycles T-n are essential for calculating new flows of incoming gases (Gin). Regarding the utility of the CP1 (CP10 or CP1$n$) and CP2 (CP20 or CP2$n$) measurements, it is the case that:

A. The CP2 pressure signal serves to adjust the total volume of gases flowing into the breathing device 200. This signal must be greater than or equal to zero during inspiration, ideally zero for the gas consumption to be exactly equal to the inspiratory need of the user 201, considering that an extra volume of gases should be administered to compensate for the flow of gases that are suctioned from the breathing device 200 by the sampler 70. In the case of contamination of the gases administered in the breathing device 200 by gases from the external environment, the pressure set point should be slightly increased. During the expiratory cycle, the CP2 pressure signal must correspond to the expiration pressure of the user 201, indicating that the flow of gases administered is zero. At the beginning of the inspiratory cycle, exceptionally, the CP2 pressure signal should be slightly positive, in order to help in the rapid substitution of the expiratory gases remaining inside the respiratory circuit 201 for the new flows administered, ensuring the inspiration of fresh and immediately administered mixtures during the entire inspiratory cycle.

B. The difference between the CP2 and CP1 pressure signals during the inspiratory cycle provides an estimate of the flow/volume that is administered, without the need for the presence of a dedicated flow sensor/transducer close to the breathing device 200, which is difficult to implement in an RM environment.

C. The CP1 concentration signal provides an estimate of delays related to the activity of the flow controllers, gas flow through the administration line, as well as the deviation of the measurement in relation to the actual content of the gases administered, when the gas sources have known compositions. These estimates allow for the correction of the CP1 measurements of concentration, and by analogy, of the CP2 measurements of concentration.

D. The difference between the concentration signals obtained in CP1 of CP2 during the inspiration allows for the detection of failures in the administration, such as those caused by leaks in the breathing device 200 (contamination of the gases administered by gases from the external environment). This differential signal helps in adjusting the CP2 pressure set point. Ideally the difference between the CP1 and CP2 concentration measurements should be zero during most of the inspiratory cycle.

E. The CP2 concentration signal during both the inspiratory and expiratory cycles serves to monitor the respiratory gases.

Merely by way of exemplification, if the user 201 is using this system from 12:00 to 12:10, it is noted that in this time period there was a plurality of previous moments of respiration T-n. So, a history of concentration and pressure signals CP0 measured at previous moments of respiration T-n was created. In this case, the control unit 50 is responsible for storing these data.

From 12:10, the control unit 50 of this system using the methodology described above will sample and measure, in real time, the first concentration and pressure signal CP10 of the flow of incoming gases Gin administered in the breathing device 200 at the current moment of respiration T0 and the second concentration and pressure signal CP20 from the flow of respiration gases Gresp within the breathing device 200 in the current moment of respiration T0.

The control unit 50 will estimate, in real time, and based on the first and second concentration and pressure signals CP10, CP20 measured at the current moment of respiration T0 and in the concentration and pressure signals CP1$n$ and CP2$n$ measured during the previous moments of respiration T-N, a new volume and a new concentration of oxygen and carbonic gas for the flow of incoming gases Gin for an immediate future inspiration moment T1, the immediate future inspiration moment T1 occurring after the current respiration moment T0.

The control unit 50 is configured to estimate the flow of incoming gases Gin and to continuously control the plurality of flow controllers 10, in order to generate at least one flow of flow gases FG1, FG2, FG3, FGn, to form the new flow of incoming gases Gin for the immediate future inspiration moment T1.

The control unit 50 then adjusts, in real time, the volume and concentration of oxygen and carbonic gas from the flow of incoming gases Gin. It is important to remember that the flow of respiration gases Gresp may be the flow of inspired or expired gases.

If the current moment of respiration T0 is a current moment of inspiration, the flow of respiration gases Gresp will be inspired. In this case, the volume and concentration of the flow of incoming gases Gin will be estimated and adjusted based on the concentration and pressure measurements, at the current moment of inspiration of the current moment of respiration T0 within the respective inspiratory cycle. Since inspiration may vary between the current moment of inspiration of the current moment of respiration T0 and the immediate future moment of inspiration T1, it is observed that real-time control will also occur within the same inspiratory cycle, which is to say, even before the user 201 expires the flow of respiration gases Gresp.

It is also important to highlight that a plurality of immediate future moments of inspiration T2, T3, Tn may occur after the immediate future moment of inspiration T1. In other words, the volume and concentration of the flow of incoming gases Gin can be adjusted several times according to the variation of inspiration within the same inspiratory cycle, before the subsequent expiration of gases.

It should be noted that the number of estimates of new flows and their adjustments are only limited by the activity response of the flow controllers 10, by the readings of the first and second concentration and pressure signals CP10, CP20 and by the processing speed of the control unit 50.

If the current moment of respiration T0 is a current moment of expiration, the flow of respiration gases Gresp will be of expiration gases. In this case, the volume and concentration of the flow of incoming gases Gin will be estimated for the beginning of the next inspiratory cycle. Of course, the current moment of expiration can be followed by a plurality of immediate future expiration moments, before the subsequent immediate future inspiration moment T1. In this case, the algorithm simply continues to improve, without the control unit 50 performing the administration of the gases.

In other words, the volume and concentration of the flow of incoming gases Gin can be estimated—but not adjusted, given that this only occurs on inspiration—several times according to the variation of expiration within the same expiratory cycle, before the consequent inspiration of gases in the immediate future moment of inspiration T1.

Having estimated the volumes and concentrations of the incoming gas flow (Gin) according to the variation of the expiration, the volume and the concentration of the flow of incoming gases (Gin) are adjusted in the immediate future moment of inspiration T1 in the next inspiratory cycle.

It should be noted that the number of estimates of new flows and their adjustments is only limited by the readings of the first and second concentration and pressure signals CP10, CP20 and by the processing speed of the control unit 50.

As previously highlighted, despite the fact that the physiological parameters S1, S2, S3, Sn are not mandatory, these can be used in conjunction with the oxygen and carbonic gas concentration and pressure signals CP10, CP20, CP1$n$ and CP2$n$ in order to improve the predictive calculation to adjust the levels of respiratory gases to be administered/inspired by the user 201. The physiological parameters S1, S2, S3, Sn can be collected at the current moment of respiration T0 and in the previous moments of respiration T-n. Similarly, anthropometric, demographic and population data can be used to improve the predictive calculation.

In the example given above, the present system and method may also take into account, for example, thoracic expansion, volume of inspired gases, electromyography and cardiac rhythm of the user 201 (physiological parameter). Thus, it would be possible to improve the algorithm of the proposed method, in order to predict, with greater accuracy, the demand for gases to be followed by the user 201.

Moreover, regarding the above example, and considering that the user 201 was a male adult, was 1.80 meters tall and weighed 80 kg, it would also be possible to cross-reference and interrelate the data of the user 201 with populational data stored in the control unit 50, to predict the respiratory responses (ratio between inspired concentrations/volumes and end-tidal levels) of the user 201 more accurately. It should be noted that these populational data comprise the cardio-respiratory behavior of individuals with certain anthropometric and demographic characteristics in breathing cycles. Having described an example of a preferred embodiment, it should be understood that the scope of the present invention encompasses other possible variations, and is only limited by the content of the claims, including their possible equivalents.

The invention claimed is:

1. Intelligent control system, based on machine learning, to modulate end-tidal concentration levels through continuous adjustments in the volume and concentration of a flow of incoming respiratory gases, said system comprising:
   a plurality of flow controllers, wherein each flow controller in the plurality of flow controllers is configured to generate at least one flow of flow gases, wherein convergence of the flow gases generates a flow of incoming gases;
   a first sensor configured to sample and measure, in real time, a first of concentration and pressure signal from the flow of incoming gases administered in a respiratory device at a current breathing moment;
   a second sensor configured to sample and measure a second concentration and pressure signal of a respiration gas flow within the respiratory device at the current respiratory moment; and
   a control unit associated with the first sensor and the second sensor, in which the control unit is configured to estimate, in real time, and based on the first and second concentration and pressure signals measured in the current moment of respiration and in the concentration and pressure signals measured in prior respiratory moments, a new volume and a new concentration of oxygen and carbonic gas for the flow of incoming gases for an immediate future inspiratory moment, the immediate future inspiratory moment occurring after the current respiratory moment,
   wherein the adjustment of the new volume and the new concentration of oxygen and carbon dioxide occurs through the activation and individual control of each of the flow controllers, and
   wherein the control unit is further configured to adjust the volume and concentration of oxygen and carbonic gas of the flow of incoming gases several times within the same inspiratory cycle.

2. The system according to claim 1, wherein the control unit is configured to estimate, in real time and through a closed loop control system, the new volume and the new concentration of oxygen and carbonic gas for the flow of incoming gases.

3. The system according to claim 2, wherein the control unit is configured to estimate the volume and concentration of the flow of incoming gases to control the level of oxygen and carbonic gas of the end-tidal/alveolar/blood gases.

4. The system according to claim 2, wherein the control unit is based on machine learning.

5. The system according to claim 2, wherein the control unit uses artificial neural networks, evolutionary algorithms or reinforcement learning.

6. The system according to claim 2, wherein the control unit uses fuzzy logic.

7. The system according to claim 1, wherein the current moment of respiration is a current inspiratory moment and the flow of respiratory gases is a flow of inspired gases.

8. The system according to claim 7, wherein a plurality of immediate future inspiratory moments occur after the immediate future inspiratory moment within the same inspiratory cycle.

9. The system according to claim 7, wherein the number of estimates of new flows and their respective adjustments are proportional to the response speeds of the plurality of flow controllers, readings of the first and second concentration and pressure signals and processing of the control unit.

10. The system according to claim 1, wherein the control unit is configured so that when the current respiratory moment occurs within an expiratory cycle, the current moment of respiration is altered to be a current moment of expiration and the flow of respiratory gases is changed to an expired gas flow.

11. The system according to claim 10, wherein a plurality of immediate future expiration moments occurs after the current expiration moment within the same expiratory cycle.

12. The system according to claim 11, wherein the control unit is configured to estimate the volume and concentration of the flow of incoming gases several times according to the variation of expiration within the same expiratory cycle.

13. The system according to claim 12, wherein the number of estimates of new flows and respective adjustments is proportional to the reading responses of the first and second concentration and pressure signals and the processing speed of the control unit.

14. The system according to claim 13, wherein the control unit is configured to estimate the volume and concentration of oxygen and carbonic gas from the flow of incoming gases for an upcoming inspiratory cycle according to the variation of the expiration within the same expiratory cycle.

15. The system according to claim 1, wherein the control unit is configured to receive and store in a memory, in real time, the first and second concentration and pressure signals and at least one physiological parameter.

16. The system according to claim 15, wherein the control unit is configured to estimate, in real time, the new volume and new concentration of oxygen and carbonic gas for the flow of incoming gases also based on at least one physiological parameter.

17. The system according to claim 15, wherein at least one physiological parameter is a parameter selected from a group composed of: thoracic expansion, volume of inspired and expired gases, electromyography, pulse oximetry, heart rhythm, respiratory gas humidity, ECG signal, blood pressure, arterial blood velocity, gasometry, blood pH, temperature and electrical conductance of the skin.

18. The system according to claim 17, wherein the control unit comprises anthropometric, demographic and population data.

19. The system according to claim 18, wherein the control unit is configured to estimate the new volume and new concentration of oxygen and carbonic gas for the flow of incoming gases also based on anthropometric, demographic and population data.

20. The system according to claim 1, wherein the plurality of flow controllers is fed individually with a mixture of oxygen, nitrogen and carbonic gas of different concentrations.

21. The system according to claim 1, wherein the control unit individually controls the flows of each of the flow controllers by sending individual signals to each controller with levels of opening gradation between 0% and 100%.

22. The system according to claim 21, wherein the plurality of flow controllers presents an actuation response of a maximum of 10 milliseconds to 90% of opening.

23. The system according to claim 1, wherein the first concentration and pressure signal and the second concentration and pressure signal are measured by sensors of concentrations of oxygen, carbonic gas and pressure that have a response time of less than 150 milliseconds (ms).

24. The system according to claim 1, wherein the breathing device is a breathing mask selected from a group ranging from a simple mask without gas leakage control to a more complex mask with leakage control, input and output valves, inspiration reservoirs, and respiratory circuits with inspiratory and/or expiratory reservoirs.

25. Intelligent control method, based on machine learning, to modulate end-tidal concentration levels through continuous adjustments in the volume and concentration of a flow of incoming respiratory gases, said method comprising:
   a) continuously sampling and measuring a first concentration and pressure signal of the incoming gas flow administered in a breathing device at the current breathing moment;
   b) continuously sampling and measuring a second concentration and pressure signal of a flow of respiration gases within the breathing device at the current moment of respiration;
   c) estimating based on the signals sampled and measured in a) and b) and in concentration and pressure signals measured at previous moments of respiration, a new volume and a new concentration of oxygen and carbonic gas for the flow of incoming gases for an immediate future inspiratory moment; and
   d) adjusting the volume and concentration of oxygen and carbonic gas in the flow of incoming gases within the same inspiratory cycle.

26. The system according to claim 25, wherein the flow of incoming respiratory gases is formed by the convergence of at least one outflow gas flow, said outflow gas flow generated from a plurality of flow controllers.

27. The system according to claim 26, wherein the adjustment of the new volume and the new concentration of oxygen and carbonic gas occurs through activation and individual control of each flow controller in the plurality of flow controllers.

* * * * *